United States Patent [19]

Mueller et al.

[11] Patent Number: 4,649,147

[45] Date of Patent: Mar. 10, 1987

[54] TREATING ELASTIN DEGRADATION WITH 1-(ALKENOYL)AZACYCLOALKYL CARBOXYLIC ACIDS AND DERIVATIVES

[75] Inventors: Richard A. Mueller, Glencoe; Richard A. Partis, Evanston, both of Ill.

[73] Assignee: G. D. Searle & Co., Skokie, Ill.

[21] Appl. No.: 752,873

[22] Filed: Jul. 8, 1985

[51] Int. Cl.$^4$ .................. A61K 31/445; C07D 211/64
[52] U.S. Cl. .................... 514/315; 514/210; 514/212; 514/330; 514/423; 540/1; 540/607; 546/245; 546/226; 548/540
[58] Field of Search .............. 548/540; 546/245, 226; 540/1, 607; 514/210, 212, 315, 330, 423

[56] References Cited

U.S. PATENT DOCUMENTS

| | | | |
|---|---|---|---|
| 3,248,396 | 4/1966 | Skav et al. | 548/540 X |
| 3,621,043 | 11/1971 | Seki et al. | 548/540 X |
| 4,118,500 | 10/1978 | Mitzlaff et al. | 548/540 X |
| 4,208,421 | 6/1980 | Morelle et al. | 548/533 X |

OTHER PUBLICATIONS

Sandberg, L. et al., *New England J. Med.*, 304, 566–579 (1981).
Werb, Z. et al., *J. Investigative Dermatology*, 79, 154s–159s (1982).
Rinaldo, J. et al., *New England J. Med.*, 306, 900–909 (1982).
Nakajima, K. et al., *J. Biol. Chem.*, 254, 4027–4031 (1979).
Reilly, C. et al., *J. Biol. Chem.*, 257, 8619–8622 (1982).
Tonnesen, M. et al., *J. Clin. Invest.*, 69, 25–30 (1982).
Wong, P. et al., *Biochem. Biophys. Res. Commun.*, 96, 1449–1454 (1980).
Turino, G. et al., *Amer. J. Med.*, 57, 493–503 (1974).
Boudier, C. et al., *J. Biol. Chem.*, 256, 10256–10258 (1981).
McDonald, J. et al., *J. Biol. Chem.*, 255, 8848–8858 (1980).
Fuller, G., *J. Med. Chem.*, 24, 651–658 (1981).
Kelley, J. et al., *J. Lab. Clin. Med.*, 96, 954–964 (1980).

*Primary Examiner*—Richard A. Schwartz
*Attorney, Agent, or Firm*—John J. McDonnell; Richard E. L. Henderson

[57] ABSTRACT

This invention relates to 1-(alkenoyl)azacycloalkyl carboxylic acids and derivatives that prevent or reduce the degradation of elastin and other proteins and that thereby prevent or retard the disease states caused by said degradation.

15 Claims, No Drawings

TREATING ELASTIN DEGRADATION WITH 1-(ALKENOYL)AZACYCLOALKYL CARBOXYLIC ACIDS AND DERIVATIVES

BACKGROUND OF THE INVENTION (a) Field of the Invention

This invention in its broadest aspect relates to protease inhibitors. In one aspect, the invention relates to certain novel methods useful in preventing or treating disease states caused by the degradative action of proteases on mammalian elastin and other proteins by administration of effective amounts of compounds of Formula I. A preferred method relates to the inhibition of the protease elastase. In other aspect, it relates to compounds of Formula I which are useful in preventing or treating disease states caused by the degradative action of proteases on mammalian elastin and other proteins.

Elastin is the functional protein component of elastic fiber tissues, a component of connective tissues. Elastic tissue is relatively rich in elastin and has a distinct rubber-like property. Most specifically, the ligamentum nuchae and the vocal chords, the vertebral ligamenta flava, the aorta, and the pulmonary arteries of some mammals are considered elastic tissues. Elastic cartilaginous tissues such as those present in the ear and epiglottis are a specialized form of elastic tissue. Lung, bronchi and skin also contain elastin and are considered elastic tissue. Sandberg, et al., *New England Journal of Medicine*, 304, 566–579 (1981).

Elastase is an elastinolytic enzyme which causes degradation and fragmentation of elastic fibers by its catalytic activity against elastin. Elastases originate from a number of sources and can be found in microorganisms, snake venoms and a number of mammalian cells and tissues including pancreas, polymorphonuclear leukocytes, and macrophages. In a normally functioning mammal, elastase is required for turnover of damaged cells and the digestion of certain invading bacteria. This invention in particular relates to the class of elastases known as the Serine Proteases.

Excessive elastin degradation has been associated with pulmonary emphysema, adult respiratory-distress syndrome, arthritis, atherosclerosis, certain skin diseases, and certain inflammatory processes leading to localized protein breakdown. Werb, et al., *Journal of Investigative Dermatology*, 79, 154S–159S, (1982); Rinaldo, et al., *New England Journal of Medicine*, 306, 900–909, (1982). By inhibiting elastase therefore it is possible to mediate, eliminate or treat a wide variety of disease conditions.

A number of inhibitors of elastase are known. Peptide chloromethyl ketones have been shown to be irreversible inhibitors of elastase. But difficulties must be considered when the in vivo use of peptide chloromethyl ketones is contemplated. The compounds are electrophiles and can react with good nucleophiles such as the thiol groups of glutathione and various proteins. During any long term treatment with these inhibitors, such non-specific alkylation could lead to the introduction of new antigenetic determinants and an autoimmune response and/or could behave similarly to the known nitrogen mustards, etc. Peptides containing aza-amino acid residues (aza peptides) are another class of inhibitors. The effectiveness of aza-peptides as elastase inhibitors depends on the rate of acylation, which in most cases is instantaneous, and also on the rate of deacylation. As such, these compounds, while useful tools in studying the in vitro properties of elastase, are still largely unsuitable for in vivo use.

(b) Information Disclosure

Certain amides of long-chain fatty acids have been disclosed in copending U.S. application Ser. No. 569,089. No compound disclosed in Serial No. '089 contains an amide nitrogen within a ring. Instead, the amide nitrogen in Ser. No. 569,089 is always attached to one or more saturated carbon atoms that is not part of a ring or attached externally to one or more aromatic rings. In contrast, the amide nitrogen of the compounds of the present invention is always included within a nonaromatic ring structure. Thus, the compounds of the present invention are clearly distinguished from the prior art.

SUMMARY OF THE INVENTION

The invention relates to a method of preventing or reducing the degradation of elastin or other proteins and thereby preventing or retarding the disease states caused by said degradation by administering compounds of the formula:

$$R^1-\overset{O}{\underset{}{C}}-N\underset{(CH_2)_m}{\overset{(CH_2)_n}{<}}\underset{CO_2R^3}{\overset{R^2}{\diagup}} \qquad I$$

wherein $R^1$ is:
  (a) alkenyl of 14 to 22 carbon atoms, inclusive;
  (b) alkadienyl of 14 to 22 carbon atoms, inclusive; or
  (c) alkapolyenyl of 14 to 22 carbon atoms, inclusive;
wherein $R^2$ is:
  (a) hydrogen; or
  (b) phenyl;
wherein $R^3$ is:
  (a) hydrogen;
  (b) alkyl of 1 to 6 carbon atoms, inclusive;
  (c) alkali metal;
  (d) alkaline earth metal; or
  (e) $NR^4R^5R^6R^{7+}$;
wherein $R^4$, $R^5$, $R^6$, and $R^7$, each being the same or different, are:
  (a) hydrogen;
  (b) alkyl of 1 to 6 carbon atoms, inclusive; or
  (c) hydroxyalkyl of 2 to 4 carbon atoms, inclusive;
wherein m is 0, 1, or 2; and
wherein n is an integer from 1 to 5, inclusive, with the proviso that the sum (m+n) is 2 to 5, inclusive.

Examples of alkyl of 1 to 6 carbon atoms, inclusive, are methyl, ethyl, propyl, butyl, pentyl, hexyl, and the isomeric forms thereof, generally referred to as lower alkyl.

Examples of hydroxyalkyl of 2 to 4 carbon atoms, inclusive, are 2-hydroxyethyl, 3-hydroxypropyl, and 4-hydroxybutyl.

Examples of alkenyl of 14 to 22 carbon atoms, inclusive, are tetradecenyl, pentadecenyl, hexadecenyl, heptadecenyl, octadecenyl, nonadecenyl, eicosenyl, heneicosenyl, docosenyl, and the isomers, including cis and trans forms, thereof.

Examples of alkadienyl of 14 to 22 carbon atoms, inclusive, are tetradecadienyl, pentadecadienyl, hexadecadienyl, heptadecadienyl, octadecadienyl, nonadecadienyl, eicosadienyl, heneicosadienyl, docosadienyl, and the isomers, including cis and trans forms, thereof.

Examples of alkapolyenyl of 14 to 22 carbon atoms, inclusive, are tetradecatrienyl, tetradecatetraenyl, pentadecatrienyl, pentadecatetraenyl, hexadecatrienyl, hexadecatetraenyl, heptadecatrienyl, heptadecatetraenyl, octadecatrienyl, octadecatetraenyl, nonadecatrienyl, nonadecatetraenyl, eicosatrienyl, eicosatetraenyl, heneicosatrienyl, heneicosatetraenyl, docosatrienyl, docosatetraenyl, and the isomers, including cis and trans forms, thereof.

Examples of alkali metal are lithium, sodium, and potassium.

Examples of alkaline earth metal are magnesium, calcium, and barium.

The compounds of this invention are prepared from azacycloalkyl carboxylates of Formula II (in which $R^2$ and $R^3$ are defined as in Formula I, above) by acylating with appropriate acyl halides ($R^1$-CO-X, in which X is a halogen) in the presence of a base.

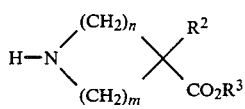

Preferred acylating conditions include reaction of the compounds of Formula II with an acyl chloride ($R^1$-COCl) in an unreactive organic solvent, such as dichloromethane, containing a tertiary amine, such as triethylamine. The azacycloalkyl carboxylates and acyl halides are readily available or may be prepared by methods well known to those skilled in the art. Salts of the acid forms of these compounds can be prepared by neutralization with the appropriate amount of an inorganic or organic base such as sodium hydroxide, potassium hydroxide, calcium hydroxide, magnesium hydroxide, ammonia, trialkylamine, dialkylamine, monoalkylamine, tris(hydroxyalkyl)amine, sodium acetate, potassium benzoate, and like bases or by direct hydrolysis of the compound wherein $R^3$ is alkyl.

The preferred embodiments of this invention include compounds of the following general structure, Formula III.

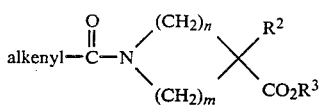

More specifically, the preferred embodiments include compounds of Formula III wherein $R^2$ is hydrogen or phenyl; wherein $R^3$ is hydrogen or alkyl of 1 to 6 carbon atoms, inclusive; wherein m is 0, 1, or 2; and wherein n is 1 to 4, inclusive, with the proviso that the sum (m+n) is 3 or 4.

The most preferred embodiments of this invention include compounds of the following general structure, Formula IV.

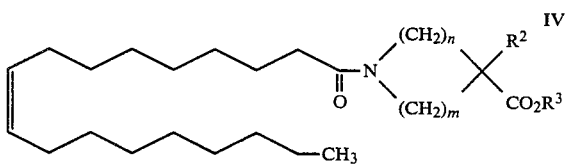

More specifically, the most preferred embodiments include compounds of Formula IV wherein $R^2$ is hydrogen or phenyl; wherein $R^3$ is hydrogen or alkyl of 1 to 6 carbon atoms, inclusive; wherein m is 0, 1, or 2; and wherein n is 1 to 4, inclusive, with the proviso that the sum (m+n) is 3 or 4.

The compounds useful in practicing the method of the invention are inhibitors of leucocyte elastase and cathepsin G. Since elastase is involved in the breakdown of elastin and subsequently involved in a number of disease states, a compound which blocks the action of elastase will be useful in the management, treatment and prevention of such diseases. Elastase, in addition to degrading elastin, also will hydrolyse methoxysuccinyl-ala-ala-pro-val-nitroanilide (MSN), a highly selective synthetic substance. Nakajima, K., et al., *J. Biol. Chem.*, 254, 4027 (1979). This is useful in measuring inhibition of elastase because the hydrolysis of MSN is easily quantitated by measuring the release of p-nitroaniline spectrophotometrically. Therefore, the degree of elastase inhibition can be readily measured by noting the rate of inhibition of the hydrolysis of MSN. The compounds of the invention are therefore tested in vitro as follows. The rate of hydrolysis of methoxysuccinyl-ala-ala-pro-val-nitroanalide by human leukocyte elastase is monitored spectrophotometrically in the presence and absence of test compound. The inhibition of the enzymatic reaction by 20% or more at a given concentration of test compound is taken as positive inhibition of elastase. $IC_{50}$ values are then determined.

During periods of active rheumatoid arthritis, vast numbers of human neutrophils are attracted to diseased joints where they engage in phagocytosis of locally generated immune complexes and tissue debris. During the process, enzymes (primarily elastase and cathespin G) are released into the joint spaces. Elastase has the capacity in this situation to degrade synovial cartilage and collagen and also contribute to joint destruction in a synergistic process with cathepsin G. Cathepsin G also causes conversion of angiotensin I to angiotensin II which is associated with inflammatory processes, Reilly, C. F., et al., *J. Biol. Chem.*, 257, 8619 (1982) and angiotensinogen to angiotensin II, Tonnesen, M. G., et al., *J. Clin. Invest.*, 69, 25 (1982). Natural elastase inhibitors (macro molecules such as in $\alpha_1$-proteinase inhibitor) already exist in normal serum and synovial fluid and may prevent precipitous joint destruction. Oxidation of the natural inhibitor (to the sulfoxide form) renders this material inactive. Wong, P. S. and J. Travis, *Biochem Biophys. Res. Commun.*, 96, 1449 (1980). Exogenous smaller molecular weight inhibitors of the invention can gain access to the micro-environments within the joint space not accessible to the natural inhibitors due to their molecular size, oxidation, charge repulsion or lipid solubility, and thereby inhibit or prevent further elastase-related destruction. In addition, pulmonary emphysema is a disease characterized by a progressive uninhibited proteolysis of lung tissue by enzymes such as elastase which in this case are released from leukocytes. People who are homozygotes in an $\alpha_1$-antitrypsin deficiency are predisposed to the disease. See, e.g., Turino, et al., *Amer. J. Med.*, 57, 493–503 (1974). The compounds of the invention could also be used to prevent the further proteolysis of lung tissue. Again, the ability of the compounds to inhibit cathepsin G is desirable, since the combination of elastase and cathepsin G has been reported to be five times as efficient at degrading elastin as is elastase alone. Boudier, C., et al., *J. Biol. Chem.*, 256, 10256 (1981). In a like manner, adult respiratory-distress syndrome, certain skin diseases, aging, and certain inflammatory processes where the disease state is connected with the localized breakdown of protein by elastase could be treated by elastase inhibitors, such as the compounds of this ivnention. For example, degradation of fibronectin, an important biological substance, could be inhibited. McDonald, J. A., and D. G. Kelley, *J. Biol. Chem.*, 255, 8848 (1980).

Fibrosis is a connective tissue disease characterized by overaccumulation of extracellular fibrous matrix components, particularly collagen. Since prolyl hydroxylation is required for active secretion and thermal stability of collagen, fibrosis could be treated by inhibitors of prolyl-4-hydroxylase, such as the compounds of this invention. See G. C. Fuller, *J. Med. Chem.*, 24, 651–658 (1981). The following procedure is used to test the compounds in vitro for prolyl-4-hydroxylase inhibition.

Purified mammalian prolyl-4-hydroxylase [EC 1.14.11.2:prolyl-glycyl-peptide, 2-oxyglutarate: oxidoreductase] is incubated with substrates (i.e., native unhydroxylated collagen of either 60,000 molecular weight, $K_m$ $10^{-8}M$; or 90,000 molecular weight, $K_m$ $10^{-11}M$), α-ketoglutarate, oxygen, and enzyme cofactors, with or without the test compounds. End-point is determined by measuring release of tritiated water during the hydroxylation of $H^3$-peptidyl proline or release of $^{14}CO_2$ formed from the coupled decarboxylation of $^{14}C$-α-ketoglutarate. Data are reported as percent inhibition with test compound at a given concentration relative to the control assays without test compound.

The procedure described by Kelley et al., *J. Lab. Clin. Med.*, 96, 954–964 (1980), is used to test the compounds in vivo for activity against bleomycin-induced lung fibrosis in male syrian hamsters. In this assay, active compounds inhibit production and accumulation of hydroxyproline in the lungs. Activities are reported as percent inhibitions at day 21 relative to untreated animals.

The compounds may also be useful in the treatment of other enzyme related diseases, such as hypercholesterolemia related to HMG CoA reductase, hypertension associated with high angiotensin II production, inflammatory bowel diseases, and the like. In addition, the compounds are cytoprotective. This invention is not limited to these examples as one skilled in the art could readily apply these methods to any protease-related disease or condition.

The method of the invention can be practiced in a variety of ways and the compounds can be administered in a number of dosage forms. A preferred method of delivery would be in such a manner so as to localize the action of the inhibitor. So, for example, in arthritis, the compounds could be injected directly into the affected joint, or for emphysema, the compounds could be inhaled using an aerosol or other appropriate spray. In any event, the compounds may be administered in any conventional manner. The compounds could be administered in oral unit dosage forms such as tablets, capsules, pills, powders or granules. They also may be administered rectally or vaginally in such forms as suppositories. They may be introduced in the forms of eyedrops, intraperitoneally, subcutaneously, or intramuscularly using forms known to the pharmaceutical art. For the treatment of inflammatory skin diseases, the compounds of the present invention may also be administered topically in the form of ointments, creams, gels or the like. Regardless of the route of administration selected, the compounds are formulated into pharmaceutically acceptable dosage forms by conventional methods known to the pharmaceutical art.

An effective but non-toxic quantity of the compound is employed in treatment. The dosage regimen for treating protease-related degradation of elastin and other proteins with the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ relatively low dosages at first, subsequently increasing the dose until a maximum response is obtained.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples, temperatures are given in degrees celcius (°C.) and quantities of materials in grams and milliliters unless otherwise noted.

DESCRIPTION OF THE PREFERRED EMBODIMENTS

EXAMPLE 1

1-(1-oxo-9Z-octadecenyl)proline

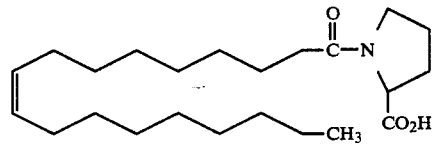

To a mixture of L-proline (25 mmole) and 25 ml of triethylamine in 100 ml of dichloromethane at room temperature was added oleoyl chloride (70 mmole). After four days the volatiles were removed under a stream of nitrogen gas. The residue was triturated with 100 ml of diethyl ether, insolubles were removed and discarded, and the filtrate was concentrated in vacuo. Column chromatography on silica gel gave analytically pure title compound.

Analysis Calcd. for $C_{23}H_{41}NO_3$: C, 72.77; H, 10.89; N, 3.69.

Found: C, 72.45; H, 10.99; N, 3.51.

EXAMPLE 2

1-(1-oxo-9Z-ocadecenyl)-3-piperidinecarboxylic acid

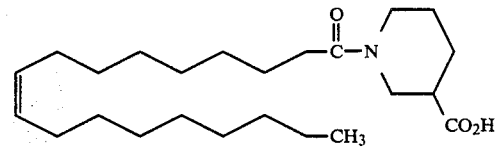

The title compound was prepared by the method of Example 1 using 3-piperidinecarboxylic acid instead of L-proline.

Analysis Calcd. for $C_{24}H_{43}NO_3$: C, 73.24; H, 11.01; N, 3.56.

Found: C, 73.18; H, 11.30; N, 3.77.

EXAMPLE 3

1-(1-oxo-9Z-octadecenyl)-4-piperidinecarboxylic acid

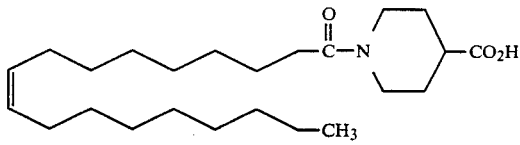

The title compound was prepared by the method of Example 1 using 4-piperidinecarboxylic acid instead of L-proline.

Analysis Calcd. for $C_{24}H_{43}NO_3$: C, 73.24; H, 11.01; N, 3.56.

Found: C, 73.02; H, 11.12; N, 3.20.

EXAMPLE 4 ethyl 1-(1-oxo-9Z-octadecenyl)-4-phenyl-4-piperidinecarboxylate

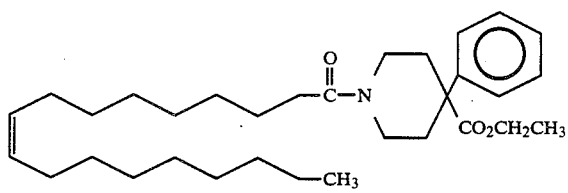

The title compound was prepared by the method of Example 1 using ethyl 4-phenyl-4-piperidinecarboxylate instead of L-proline.

Analysis Calcd. for $C_{32}H_{51}NO_3$: C, 77.22; H, 10.33; N, 2.81.

Found: C, 76.91; H, 10.32; N, 2.77.

EXAMPLE 5

1-(1-oxo-9Z-octadecenyl)-4-phenyl-4-piperidinecarboxylic acid

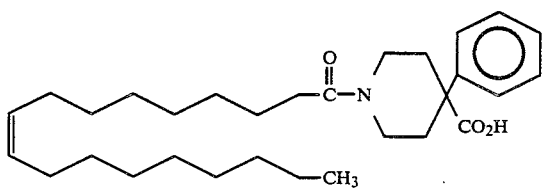

Later chromatographic fractions from the chromatography of Example 4 afforded the analytically pure carboxylic acid as a minor component, m.p. 106°–109°.

Analysis Calcd. for $C_{30}H_{47}NO_3$: C, 76.71; H, 10.09; N, 2.98.

Found: C, 76.72; H, 9.99; N, 3.02.

EXAMPLE 6

1-(1-oxo-9Z-octadecenyl)proline methyl ester

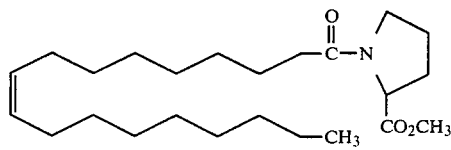

To 1.0 g of the title product of Example 1 in dichloromethane was added an excess of diazomethane in diethyl ether. After about ten minutes, volatiles were removed in vacuo to give an oil. Chromatography on silica gel (using ethyl acetate-hexane as eluent) gave analytically pure title compound.

Analysis Calcd. for $C_{24}H_{43}NO_3$: C, 73.23; H, 11.01; N, 3.56.

Found: C, 73.17; H, 11.03; N, 3.41.

EXAMPLE 7

| Compound [Product of Example Number] | Elastase Inhibition $IC_{50}$ (mcM) | Prolyl-4-hydroxylase Inhibition $IC_{50}$ (mcM) | Bleomycin-induced Fibrosis | |
|---|---|---|---|---|
| | | | % Inhib. of Lung wt./body wt. (Dose, mg/kg) | % Inhib. of Hydroxyproline (Dose, mg/kg) |
| 1 | 7.8 | 4.4 | | |
| 2 | 3.4 | 5.9 | | |
| 3 | 4.6 | 9.0 | | |
| 4 | # | | | |
| 5 | 1.2 | | | |
| 6 | | | 33.0 (100 mg/kg) | 30.1 (100 mg/kg) |

Table of Pharmacological Test Results.

22% inhibition against elastase at 20 mcM.

What is claimed is:

1. A compound of the formula:

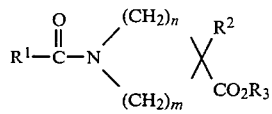

wherein $R^1$ is:
 (a) alkenyl of 14 to 22 carbon atoms, inclusive;
 (b) alkadienyl of 14 to 22 carbon atoms, inclusive; or
 (c) alkapolyenyl of 14 to 22 carbon atoms, inclusive;
wherein $R^2$ is:
 (a) hydrogen; or
 (b) phenyl;
wherein $R^3$ is:
 (a) hydrogen;
 (b) alkyl of 1 to 6 carbon atoms, inclusive;
 (c) alkali metal;
 (d) alkaline earth metal; or
 (e) $NR^4R^5R^6R^{7+}$;
wherein $R^4$, $R^5$, $R^6$, and $R^7$, each being the same or different, are:
 (a) hydrogen;
 (b) alkyl or 1 to 6 carbon atoms, inclusive; or
 (c) hydroxyalkyl of 2 to 4 carbon atoms, inclusive;
wherein m is 0, 1, or 2; and
wherein n is an integer from 1 to 5, inclusive, with the proviso that the sum (m+n) is 2 to 5, inclusive.

2. A compound according to claim 1 having the formula:

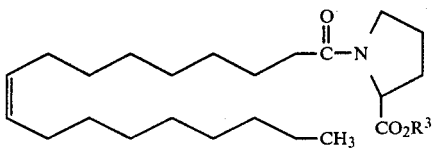

wherein $R^3$ is:
(a) hydrogen;
(b) alkyl of 1 to 6 carbon atoms, inclusive.

3. A compound according to claim 2, which is 1-(1-oxo-9Z-octadecenyl)proline.

4. A compound according to claim 2, which is 1-(1-oxo-9Z-octadecenyl)proline methyl ester.

5. A compound according to claim 1 having the formula:

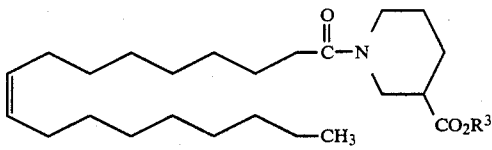

wherein $R^3$ is:
(a) hydrogen;
(b) alkyl of 1 to 6 carbon atoms, inclusive.

6. A compound according to claim 5, which is 1-(1-oxo-9Z-octadecenyl)-3-piperidinecarboxylic acid.

7. A compound according to claim 1 having the formula:

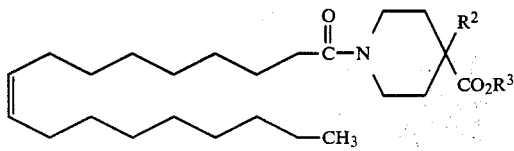

wherein $R^2$ is:
(a) hydrogen; or
(b) phenyl;
wherein $R^3$ is:
(a) hydrogen;
(b) alkyl of 1 to 6 carbon atoms, inclusive.

8. A compound according to claim 7, which is 1-(1-oxo-9Z-octadecenyl)-4-piperidinecarboxylic acid.

9. A compound according to claim 7, which is 1-(1-oxo-9Z-octadecenyl)-4-phenyl-4-piperidinecarboxylic acid.

10. A compound according to claim 7, which is ethyl 1-(1-oxo-9Z-octadecenyl)-4-phenyl-4-piperidinecarboxylate.

11. A pharmaceutical composition for treating protease-induced degradation of elastin and other proteins in mammals comprising a therapeutically effective amount of at least one compound according to claim 1, together with one or more non-toxic pharmaceutically acceptable carriers.

12. A pharmaceutical composition according to claim 11 wherein said compound is selected from the group consisting of:
1-(1-oxo-9Z-octadecenyl)proline,
1-(1-oxo-9Z-octadecenyl)proline methyl ester,
1-(1-oxo-9Z-octadecenyl)-3-piperidinecarboxylic acid,
1-(1-oxo-9Z-octadecenyl)-4-piperidinecarboxylic acid,
1-(1-oxo-9Z-octadecenyl)-4-phenyl-4-piperidinecarboxylic acid, and
ethyl 1-(1-oxo-9Z-octadecenyl)-4-phenyl-4-piperidinecarboxylate.

13. A method for treating protease-induced degradation of elastin and other proteins in mammals comprising administering a therapeutically effective amount of at least one compound of claim 1 to a mammal in need of such treatment.

14. A method according to claim 13 wherein said compound is selected from the group consisting of:
1-(1-oxo-9Z-octadecenyl)proline,
1-(1-oxo-9Z-octadecenyl)proline methyl ester,
1-(1-oxo-9Z-octadecenyl)-3-piperidinecarboxylic acid,
1-(1-oxo-9Z-octadecenyl)-4-piperidinecarboxylic acid,
1-(1-oxo-9Z-octadecenyl)-4-phenyl-4-piperidinecarboxylic acid and
ethyl 1-(1-oxo-9Z-octadecenyl)-4-phenyl-4-piperidinecarboxylate.

15. A method for treating protease-induced degradation of elastin and other proteins in mammals comprising administering a therapeutically effective amount of a pharmaceutical composition of claim 11 to a mammal in need of such treatment.

* * * * *

UNITED STATES PATENT OFFICE
CERTIFICATE OF CORRECTION

PATENT NO. : 4,649,147
DATED : March 10, 1987
INVENTOR(S) : Mueller et al.

It is certified that error appears in the above-identified patent and that said Letters Patent are hereby corrected as shown below:

In the formula in claim 1, that portion of the formula reading "$CO_2R_3$" should read -- $CO_2R^3$ --.

Signed and Sealed this

Twenty-second Day of December, 1987

Attest:

DONALD J. QUIGG

*Attesting Officer*  *Commissioner of Patents and Trademarks*